United States Patent [19]

Bayssat et al.

[11] 4,224,341

[45] Sep. 23, 1980

[54] 5-SUBSTITUTED INDAN-2 CARBOXYLIC ACID AND FUNCTIONAL DERIVATIVES

[75] Inventors: Michel Bayssat, Charbonnieres; Francis Sautel, Lyons; Jean-Claude Depin, Lyons; Annie Betbeder Matibet, Lyons, all of France

[73] Assignee: Lipha, Lyonnaise Industrielle Pharmaceutique, Lyons, France

[21] Appl. No.: 860,466

[22] Filed: Dec. 14, 1977

Related U.S. Application Data

[63] Continuation-in-part of Ser. No. 756,862, Jan. 4, 1977, abandoned.

[30] Foreign Application Priority Data

Jan. 12, 1976 [FR] France ............................... 76 00552
Dec. 14, 1976 [FR] France ............................... 76 37754
Nov. 18, 1977 [FR] France ............................... 77 33496

[51] Int. Cl.$^2$ ..................... C07C 65/20; C07C 69/95; A61K 31/19; A61K 31/215

[52] U.S. Cl. ................................ 424/308; 260/559 R; 260/558 R; 250/558 A; 260/558 P; 260/558 S; 260/556 B; 260/556 C; 560/10; 560/21; 560/36; 560/51; 560/52; 562/428; 562/436; 562/441; 562/460; 562/462; 424/309; 424/317; 424/319; 424/321; 424/324

[58] Field of Search ............... 560/52, 36, 10, 12, 560/51, 21; 562/460, 462, 428, 441, 436; 424/308, 317, 324, 309, 319, 321; 260/558 A, 558 R, 558 P, 558 S, 556

[56] References Cited

U.S. PATENT DOCUMENTS 3,953,500 4/1976 Noguchi et al. .................. 560/52
4,057,573 11/1977 Haas et al. ........................ 560/52

FOREIGN PATENT DOCUMENTS 849285 6/1977 Belgium.

OTHER PUBLICATIONS

Kirsch et al., Ann. 1976, pp. 1914–1924.
Noguchi et al., Japan Kokai 74-80053, as cited in Chem. Abstracts 82, 15594f (1975).

*Primary Examiner*—Jane S. Myers
*Attorney, Agent, or Firm*—Browdy and Neimark

[57] ABSTRACT

5-Substituted indan-2-carboxylic acids and functional derivatives thereof having inflammation-reducing properties have the general formula

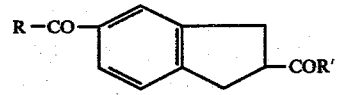

in which R is a phenyl, phenyl-lower alkenyl, phenyl-lower alkyl, phenyl substituted by at least one of the halogens, lower alkyl, lower alkoxy, acetamido, amino, lower dialkylamino, nitro, phenyl, lower alkylsulfonyl, lower dialkylaminosulfonyl and sulfamido, cyclohexyl, furyl, lower alkylfuryl, thienyl, halothienyl, lower alkylthienyl, or pyridyl group and R' is a hydroxyl, lower alkoxy, lower dialkylaminoalkoxy, cinnamoylamido lower alkoxy, 2-hydroxyethylamino, amino or lower dialkylaminoalkyl amino group. Besides the esters and amides, the functional derivatives of the acids include the pharmacologically acceptable salts of the above compounds. The compounds are also of low toxicity, have analgesic activity and exert an antipyretic effect.

12 Claims, No Drawings

5-SUBSTITUTED INDAN-2 CARBOXYLIC ACID AND FUNCTIONAL DERIVATIVES

CROSS-REFERENCE TO RELATED APPLICATIONS

The present application is a continuation-in-part of U.S. application Ser. No. 756,862, filed Jan. 4, 1977, now abandoned, the entire contents of which are hereby incorporated by reference.

FIELD OF THE INVENTION

This invention relates to new derivatives of indan, to methods of preparing the same, and to their use as medicaments.

DESCRIPTION OF THE PRIOR ART

The inflammation-reducing properties of certain 5-cycloalkyl-indan-1-carboxylic acids are known, as also are the inflammation-reducing and analgesic properties of alkyl or acylindan-1-carboxylic acids. Finally, it is also known that certain 6-acyl-indan-2-carboxylic acids have lipidemia-reducing properties.

SUMMARY OF THE INVENTION

In accordance with the invention, new 5-cycloalkyl, 5-aryl and 5-heteroaroyl indan-2-carboxylic acids have been prepared and their remarkable inflammation reducing, analgesic and antipyretic properties have been discovered.

GENERAL DESCRIPTION OF THE INVENTION

The acids of the present invention are represented by the general formula

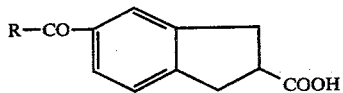

(I)

in which R is an aryl, a heteroaryl or a cycloalkyl group.

R may be a phenyl, a phenyl-lower alkyl or a phenyl-lower alkenyl group, a substituted phenyl group, a furyl group, a thienyl group (which may be substituted, preferably monohalothienyl), a pyridyl group or a cyclohexyl group.

When R is a phenyl group, it may be substituted by one or more halogen atoms, lower alkyl, lower alkoxy, acetamido, amino, dialkylamino, nitro, phenyl, alkylsulfonyl, dialkylaminosulfonyl or sulfamido groups.

When R is a substituted thienyl group, there is at least one substituent chosen from the halogen atoms and lower alkyl groups.

Preferably, when R is a phenyl radical, it is substituted by at least one substituent chosen from chlorine and the acetamido, dimethylamino, methylsulfonyl, dimethylaminosulfonyl and sulfamido radicals, and when R is a substituted thienyl radical, it is substituted by at least one substituent chosen from chlorine and the methyl radical. When R is a furyl radical, it is substituted by a methyl radical.

Specific and non-limiting preferred examples of the acids in accordance with the present invention include 5-(p-dimethylaminobenzoyl)-indan-2-carboxylic acid, 5-(p-methylsulfonylbenzoyl)-indan-2-carboxylic acid, 5-(p-sulfamidobenzoyl)-indan-2-carboxylic acid, 5-(p-dimethylaminosulfonylbenzoyl)-indan-2-carboxylic acid, 5-(4'-acetamido-3'-chlorobenzoyl)-2-carboxylic acid, 5-(3'-methyl-2'-thenoyl)-indan-2-carboxylic acid, 5-(4',5'-dichloro-2'-thenoyl)-indan-2-carboxylic acid, and 5-(5'-methyl-2'-furoyl)-indan-2-carboxylic acid.

Derivatives of these acids in the form of therapeutically acceptable salts or the esters such as the lower aliphatic esters, the amino-esters such as the lower dialkylamino-loweralkyl esters and the cinnamic esters, and in the form of amides such as the carboxamides, which may be substituted on the nitrogen atom, are therapeutically useful and constitute a part of the invention.

Preferred esters are the lower aliphatic esters, and, particularly when R is thenyl or furyl, the lower dialkylaminoalkyl esters, for example, 2'-(N,N-diethylaminoethyl) 5-(2'-thenoyl)-indan-2-carboxylate and 2'-(N,N-diethylaminoethyl) 5-(2'-furoyl)-indan-2-carboxylate.

Preferred amides include the lower alkylamino-loweralkyl amides derived from carboxylic acids represented by general formula I in which R is a phenyl radical which can be substituted by up to two halogen atoms, or a thienyl radical. Specific and non-limiting preferred examples of such carboxamides are the diethylaminocarboxamides such as N-[2'-(N',N'-diethylaminoethyl)] 5-benzoyl-indan-2-carboxamide, N-[2'-(N',N'-diethylaminoethyl)] 5-(2'-thenoyl)-indan-2-carboxamide and N-[2'-(N',N'-diethylaminoethyl)] 5-(2',5'-dichlorobenzoyl)-indan-2-carboxamide.

Throughout the present specification and claims the term lower alkyl, as well as the term alkyl, unless otherwise specified, refers to $C_1$-$C_5$ alkyl.

The compounds of the present invention may be obtained by a variety of synthetic procedures.

METHOD A

The compounds can be obtained by alkaline hydrolysis of an ester having the general formula IV. The starting material is an ester having the general formula II in which R' if preferably a lower alkyl group

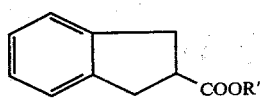

(II)

(a) An aroyl halide having the general formula III

 (III)

in which R is as defined above and X is a halogen, is reacted with the ester of general formula II under Friedel - Crafts conditions.

The reaction may be performed with or without a solvent, but preferably using a suitable solvent such as methylene chloride or carbon disulphide, etc., at a temperature between 0° C. and the boiling point of the solvent and preferably at the reflux temperature of the solvent. Among the Lewis acids which may be used under Friedel-Crafts conditions, anhydrous aluminum chloride is preferred. The reactants employed may be present in stoichiometric quantities or in excess, but preferably there is an excess of the aroyl halide and of aluminum chloride, which excess may be as much as 400%.

(b) An excess of ester II is reacted with an aroyl halide having the general formula III in the presence of a catalytic quantity of zinc oxide. An excess of ester II as great as 100% may be present and the reaction preferably takes place in the absence of a solvent at the reflux temperature of the reaction mixture.

In this way there are obtained the compounds having the general formula IV

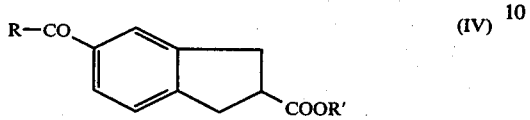 (IV)

in which R and R' are as above defined.

To obtain the acids of general formula I it is merely necessary to subject the compounds of general formula IV to hydrolysis under alkaline conditions. The bases which may be used include soda and potash and they are used in an aqueous alcoholic medium, for example, at temperatures between ambient temperature and the reflux temperature of the reaction mixture. The bases are used in stoichiometric proportion or in excess, preferably in excess, and the proportion of alkanol may be up to 100%. The hydrolysis product is then acidified to liberate the acid.

For the compounds wherein R is a phenyl group substituted by a sulfamido or dimethylsulfamido radical, an ester of formula (IV) is the starting point in which R' is a lower alkyl group and R is a phenyl group substituted by an amino radical. This ester is subjected to diazotization by techniques known of themselves, after which the aryldiazonium salt obtained is treated with a solution of sulfur dioxide in acetic acid in the presence of a copper salt, preferably cupric chloride, in order to obtain a compound of formula (IV) in which R' has the same meaning as above and R is a phenyl radical appropriately substituted by a chlorosulfonyl radical.

When the latter is treated with gaseous ammonia or ammonia in a water or lower alkanol solution, the compound of formula (IV) is obtained wherein R is a phenyl radical substituted by a sulfamido radical. If the ammonia is replaced by dimethylamine, a compound with formula (IV) is obtained wherein R is a phenyl radical substituted by a dimethylsulfamido radical.

For the compounds wherein R is a phenyl radical substituted by a dimethylamino radical, a compound of formula (IV) in which R' is a lower alkyl group and R is a phenyl radical substituted by an amino radical is treated with formaldehyde in its monomeric form, either pure or in a water solution, in the presence of hydrogen and of a hydrogenation catalyst, preferably palladium on carbon at an appropriate temperature.

In this way compounds with formula (IV) are obtained for which R is a phenyl group substituted by a dimethylamino radical, R' having the same meaning as before.

Finally, when R is a radical substituted by at least one halogen, these compounds are obtained by treating a compound of formula (IV) in which R is a phenyl, thienyl, or monosubstituted furyl radical and R' has the same meaning as before, with a halogen solution in acetic acid, this solution being either saturated or unsaturated and the reaction taking place at temperatures between ambient temperature and the reflux temperature.

METHOD B

In the first step an appropriately substituted orthoxylene having the general formula V

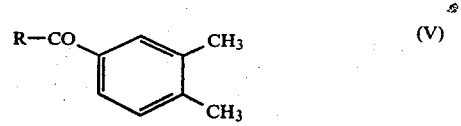 (V)

is prepared by either of the procedures (a) or (b) described under Method A.

Using as starting materials compounds having the general formula V there are first obtained compounds having the general formula VI:

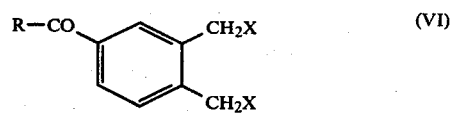 (VI)

in which R is as above defined and X is a halogen atom, preferably bromine, either by the direct action of a halogen on a compound of general formula V whilst irradiating with ultra-violet light and preferably at the reflux temperature of the mixture, or, in the case of bromine, by the action of N-bromosuccinimide on a compound of the general formula V in solution in a suitable solvent such as carbon tetrachloride, and in the presence of a catalyst such as an organic peroxide, preferably benzoyl peroxide, or of $\alpha,\alpha'$-azobisisobutyronitrile whilst irradiating with ultra-violet light. The reaction is generally carried out at temperatures between ambient temperature and the boiling point of the solvent and preferably under reflux.

Compounds having the general formula VII

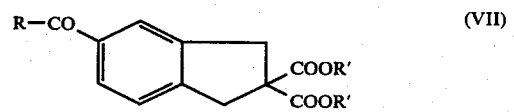 (VII)

in which R is as above defined and R' is a lower alkyl group, are obtained from compounds having the general formula VI by the reaction therewith of a malonic ester having the general formula

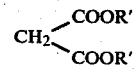

in which R' is as defined above, in the presence of an alkali metal alkanolate dissolved in a lower alkanol or in ethyl carbonate, preferably in ethyl carbonate, and at temperatures between ambient temperature and the reflux temperature of the solvent and preferably under reflux.

The acids having the general formula VIII, in which R is as above defined

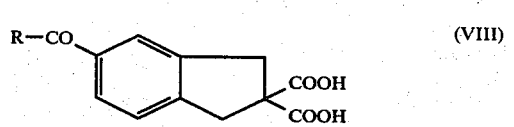 (VIII)

are obtained from the esters having the general formula VII by alkaline hydrolysis in an aqueous alcoholic medium at temperatures between ambient temperature and the reflux temperature, and preferably at the latter. The bases which may be used for this hydrolysis are preferably potash or soda, and they are used in proportions which may be between the stoichiometric proportion and a 100% excess and are preferably used in a 100% excess. The proportion of lower alkanol in the aqueous alcohol mixture may be up to 100%.

The compounds having the general formula I are obtained from acids having general formula VIII by subjecting the latter to decarboxylation by a known method, for example, by heating the diacid to its melting point or by heating the diacid to reflux in a hydracid such as concentrated hydrochloric acid.

As an alternative, the esters having general formula VII may be directly decarboxylated to compounds of general formula IV by heating the esters in dimethyl sulphoxide in the presence of water and of sodium chloride at temperatures between 120° C. and the reflux temperature of the solvent.

METHOD C

In this method, a solution of a Grignard reagent is prepared in known manner in a suitable solvent such as diethyl ether or tetrahydrofuran, for example, by reacting a metal such as magnesium or lithium, and preferably magnesium, with an appropriately substituted halo-orthoxylene having the general formula:

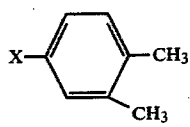

in which X is a halogen atom.

The solution of Grignard reagent is then reacted with an aroyl halide having the general formula III dissolved in a solvent such as diethyl ether or tetrahydrofuran at a temperature between 0° C. and the reflux temperature of the solvent used, preferably at the reflux temperature of the solvent.

After acid hydrolysis and the appropriate processing, there is thus obtained a compound having the general formula V which is then submitted to the same series of reactions as described for method B.

The pharmacological inflammation reducing, analgesic and antipyretic activities of the compounds according to the present invention have been demonstrated in animal experimentation. The examples are not limiting.

A—The substances are of low toxicity. For example, the LD 50 value (oral route), determined in mice, of various compounds in accordance with the present invention are shown in column A of Table I.

B—Analgesic activity in the mouse was determined by the method of Koster et al. (Fed. Proc. 1959, Vol. 18, page 412). The active dose 50 ($AD_{50}$) value for various compounds in accordance with the present invention was determined, namely, that dose which, when administered orally, reduces by 50% the spasms of pain caused by the intraperitoneal injection of a solution of acetic acid. Results are shown in column B of Table I.

C—The anti-inflammatory activity was demonstrated by the carrageenin-induced edema test of Winter et al. (Proc. Exp. Biol. Med., Volume 111, pages 544–47). The protection afforded, by oral administration of the compound to a rat against edema induced by injecting a suspension of carrageenin under the arch of the foot of the animal was investigated. The $AD_{30}$ dose is that which inhibits the edema by 30%. Results are shown in column C of Table I.

D—The protective effect against inflammation resulting from exposure to radiation was determined in albino guinea pigs using the method of Winder et al (Arch. Inv. Pharmacodyn. 1958, Vol. 116, page 261). The $AD_{50}$ value was determined for the test substance, namely the amount which, when administered to the animal orally, reduced by 50% the erythema produced by exposing the shaved dorsal skin of the guinea pig to ultra violet radiation. Results are shown in column D of Table I.

E—The anti-inflammatory activity was also determined by the aggregation-inhibiting effect of the compounds in accordance with the present invention, in vitro, on platelets the aggregation of which was induced by collagen, in accordance with the method of Born. It is known that compounds which inhibit the activity or quantity of prostaglandin synthetase will inhibit the formation of prostaglandin $PGE_2$ and the inflammatory and pyretic effect thereof. Since prostaglandin $PGE_2$ also causes an increase in platelet aggregation, this test is an effective indication of anti-inflammatory and anti-pyretic activity due to inhibition of prostaglandin synthetase. Column E of Table I shows the minimal active concentration in γ/ml of various compounds in accordance with the present invention.

TABLE I

|  | A $LD_{50}$ mg/kg | B Acetic Acid $AD_{50}$ mg/kg | C Carrageenin $AD_{30}$ mg/kg | D U.V. $AD_{50}$ mg/kg | E Platelet Aggregation Induced By Collagen γ/ml |
|---|---|---|---|---|---|
| 5-benzoyl-indan-2-carboxylic acid | 2,100 | 40 | 18 | 40 | 2.5 |
| 5-(4'-methoxybenzoyl)-indan-2-carboxylic acid | 650 | 6 | 13 | 34 | 2.5 |
| methyl 5-(4'-dimethylaminobenzoyl)-indan-2-carboxylate | 1,450 | 2.5 | 12 | 24 | 0.25 |
| methyl 5-(2'-furoyl)-indan-2-carboxylate | 3,200 | 9 | 13 | 19 | 1 |
| 5-(2'-furoyl)-indan-2-carboxylic acid | 1,000 | 11 | 23 | 14 | 1 |
| 5-(2'-thenoyl)-indan-2-carboxylic acid | 1,200 | 6.5 | 10 | 21 | 2.5 |
| 5-(3'-furoyl)-indan-2-carboxylic acid | 2,400 | 16 | 20 | 18 | 5 |

TABLE T-continued

|  | A<br>LD$_{50}$<br>mg/kg | B<br>Acetic Acid<br>AD$_{50}$<br>mg/kg | C<br>Carrageenin<br>AD$_{30}$<br>mg/kg | D<br>U.V.<br>AD$_{50}$<br>mg/kg | E<br>Platelet<br>Aggregation<br>Induced By<br>Collagen<br>Y/ml |
|---|---|---|---|---|---|
| 5-(5'-methyl-2'-thenoyl)-indan-2-carboxylic acid | 3,000 | 12 | 7.5 | 14 | 1 |
| 5-(3'-methyl-2'-thenoyl)-indan-2-carboxylic acid | 1,200 | 37 | 26 | 25 | 10 |
| 5-(5'-methyl-2'-furoyl)-indan-2-carboxylic acid | 2,400 | 8 | 10 | 16 | 1 |
| 5-(p-dimethylaminobenzoyl)-indan-2-carboxylic acid | 960 | 3 | 14 | 20 | 0.5 |
| 5-(p-methylsulfonylbenzoyl)-indan-2-carboxylic acid | 2,800 | 35 | 40 | 10 | 1 |
| 5-(p-sulfamindobenzoyl)-indan-2-carboxylic acid | >3,200 | 25 | 43 | 90 | 5 |
| 5-(p-dimethylaminosulfonylbenzoyl)-indan-2-carboxylic acid | 2,600 | 80 | 160 | >300 | 10 |
| ethyl 5-(4'-acetamido-3'-chlorobenzoyl)-indan-2-carboxylate | 3,200 | 35 | 60 | 80 | 5 |
| 5-(4',5'-dichloro-2'-thenoyl)-indan-2-carboxylic acid | 180 | 30 | 42 | 90 | 7.5 |
| 2'-(N,N-diethylaminoethyl) 5-(2'-thenoyl)-indan-2-carboxylate, hydrochloride | 2,160 | 4 | 8 | 10 | 0.25 |
| 2'-(N,N-diethylaminoethyl) 5-(2'-furoyl)-indan-2-carboxylate, hydrochloride | 1,200 | 8 | 18 | 20 | 1 |
| N-[2'-(N',N'diethylaminoethyl)] 5-benzoyl-indan-2-carboxamide, oxalate | 1,100 | 30 | 9 | 25 | 2.5 |
| N-[2'-(N',N'-diethylaminoethyl)] 5-(2'-thenoyl)-indan-2-carboxamide, oxalate | 660 | 2.5 | 8 | 10 | 0.25 |
| N-[2'-(N',N'-diethylaminoethyl)] 5-(2',5'-dichlorobenzoyl)-indan-2-carboxamide, oxalate | 720 | 15 | 25 | 50 | 2.5 |

Therapeutic compositions consisting of at least one compound according to the present invention as an active ingredient, together with a solid or liquid pharmaceutical excipient or diluent, may be in the form of tablets, injectable solutions, suppositories or the like.

| Example of formulation | |
|---|---|
| 5-Benzoyl-indan-2-carboxylic acid | 200 mg |
| Excipients: | |
| Lactose | 30 mg |
| Wheat starch | 29 mg |
| Talc | 10 mg |
| Gelatin | 5 mg |
| Alginic acid | 20 mg |
| Fecula | 5 mg |
| Magnesium stearate | 1 mg |
| For a tablet weighing | 300 mg |

Therapeutic compositions containing an indan derivative according to the invention as their active ingredient are effective for reducing inflammation, as analgesics and antipyretics in unit doses of from 50 to 500 mg. The dosage may be adjusted to obtain the optimum therapeutic effect.

DETAILED DESCRIPTION OF PREFERRED EMBODIMENTS

The following non-limitative examples illustrate the preparation of the compounds of the present invention.

Example No. 1

Methyl 5-benzoyl-indan-2-carboxylate

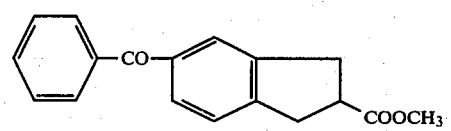

Empirical formula $C_{18}H_{16}O_3$
Molecular weight = 280.31

In a 250 cm$^3$ reaction vessel fitted with a stirrer, a cooler, a dropping funnel and a thermometer, is placed 23.2 g (0.173 mole) of anhydrous aluminum chloride in suspension in 40 ml of methylene chloride. 35.3 g (0.252 mole) of benzoyl chloride dissolved in 40 cm$^3$ of methylene chloride is then slowly added at ambient temperature. The aluminum chloride tends to pass into solution while the temperature gradually rises several degrees. The mixture is cooled to hold the temperature close to 20° C. and a solution of 11.1 g (0.063 mole) of methyl indane-2-carboxylate dissolved in 50 cm$^3$ of methylene chloride is added. The temperature gradually rises during the course of the addition and the mixture turns a light brown color. The mixture is stirred for one hour at ambient temperature and is then heated to reflux for 3 hours. After cooling, the mixture is poured into acidified iced water and the resulting mixture is extracted with chloroform. The chloroform extract is then washed with water containing caustic soda, then with slightly acidified water and finally with water. It is dried over anhydrous sodium sulphate. The product is then filtered and the filtrate concentrated to an oily residue which is distilled and a fraction is collected boiling at 178°–184° C. at 0.6 to 0.8 torr.

Example No. 2

5-benzoyl-indan-2-carboxylic acid

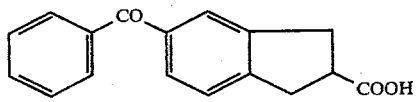

Empirical formula $C_{17}H_{14}O_3$
Molecular weight = 266.28

To a 100 cm$^3$ reaction vessel equipped with a stirrer and a cooler are successively added: 2.2 g (0.026 mole+50%) of potash dissolved in 40 cm$^3$ of water and 7.3 g (0.026 mole) of methyl 5-benzoyl-indane-2-carboxylate dissolved in 40 cm$^3$ of methanol. The mixture is heated at reflux temperature for 1 hour, the methanol evaporated and the mixture diluted with water; the alkaline mixture is then washed with ether and then acidified by the addition of hydrochloric acid. A precipitate forms which is filtered, washed with water and dried. After recrystallization from ethyl acetate the melting point is steady at 140°–142° C. (in a capillary tube).

| Acid Value | | |
|---|---|---|
| Theoretical: 210 | Found: 201 | |
| Analysis | C % | H % |
| Calculated | 76.67 | 5.30 |
| Found | 76.65 | 5.21 |

Infra-red spectrum
 $\mu$OH: 3100 to 2500 cm$^{-1}$
 $\mu$CO: 1700 cm$^{-1}$
 $\mu$CO: 1645 cm$^{-1}$
NMR Spectrum
 1 acid proton at 11.66 ppm
 Spread from 8 aromatic protons at 7.6 ppm
 5 indan protons at 3.4 ppm
The following were also prepared by the methods described in Examples 1 and 2.

5-(4'-Chlorobenzoyl)-indan-2-carboxylic acid

Empirical formula $C_{17}H_{13}ClO_3$
Melting point=183.5°–185° C. (capillary tube)

| Acid Value | | | |
|---|---|---|---|
| Theoretical = 186 | Found = 170 | | |
| Analysis | C % | H % | Cl % |
| Calculated | 67.89 | 4.36 | 11.79 |
| Found | 68.0 | 4.58 | 11.63 |

Infra-red spectrum
 $\mu$CO acidic: 1695 cm$^{-1}$
 $\mu$CO ketonic: 1650 cm$^{-1}$
 Two adjacent aromatic hydrogen atoms: 840 cm$^{-1}$
Methyl ester:
 Empirical formula $C_{18}H_{15}ClO_3$
 Melting point=79°–80° C. (capillary tube)
 Boiling point at 0.3 torr: 185° C.

| Analysis | C % | H % | Cl % |
|---|---|---|---|
| Calculated | 68.68 | 4.80 | 11.26 |
| Found | 68.44 | 4.87 | 11.50 |

Infrared spectrum:
 $\mu$CO at 1720 cm$^{-1}$ 5-(4'-Methylbenzoyl)-indan-2-carboxylic acid Empirical formula $C_{18}H_{16}O_3$
Melting point=166°–168° C. (capillary tube)
Infrared spectrum:
 $\mu$CO: 1700–1650 cm$^{-1}$

| Analysis | C % | H % |
|---|---|---|
| Calculated | 77.13 | 5.75 |
| Found | 76.99 | 5.95 |

5-(3'-Chlorobenzoyl)-indan-2-carboxylic acid

Empirical formula $C_{17}H_{13}ClO_3$
Melting point=127°–128° C. (capillary tube)

| Acid Value: | | |
|---|---|---|
| Theoretical = 186 | Found = 166 | |
| Infrared spectrum: | | |
| $\mu$CO: 1730 cm$^{-1}$ | | |
| $\mu$CO: 1650 cm$^{-1}$ | | |
| Analysis: | C % | H % | Cl % |
| Calculated | 67.89 | 4.36 | 11.79 |
| Found | 67.90 | 4.40 | 11.84 |

5-(3'-Methylbenzyl)-indan-2-carboxylic acid

Empirical formula $C_{18}H_{16}O_3$
Melting point=96°–99° C. (capillary tube)

| Acid Value: | Thehoretical = 200 | Found = 198 |
|---|---|---|
| Infrared spectrum: | | |
| $\mu$CO = 1730 cm$^{-1}$ | | |
| $\mu$CO = 1655 cm$^{-1}$ | | |
| Analysis: | C % | H % |
| Calculated | 77.13 | 5.75 |
| Found | 76.98 | 5.98 |

The ethyl ester: Boiling point at 0.45 torr=190° C.; $n_D$19.5:1.5769.
Infrared spectrum:
 $\mu$CO ester: 1740 cm$^{-1}$
 $\mu$CO ketone: 1660 cm$^{-1}$ Methyl 5-(4'-nitrobenzoyl)-indan-2-carboxylate Empirical formula $C_{18}H_{15}NO_5$
Melting point: 126°–128° C. (capillary tube)
Infrared spectrum:
 $\mu$CO acid: 1740 cm$^{-1}$
 $\mu$CO ketone: 1660 cm$^{-1}$
 Two adjacent aromatic hydrogen atoms: 850 cm$^{-1}$

| Analysis: | C % | H % | N % |
|---|---|---|---|
| Calculated | 66.45 | 4.65 | 4.31 |
| Found | 66.60 | 4.60 | 4.36 |

5-(2'-Methylbenzoyl)-indan-2-carboxylic acid

Empirical formula $C_{18}H_{16}O_3$
Melting point = 110°–112° C. (capillary tube)

| Acid Value: | Calculated = 200 | Found = 204 |
|---|---|---|

Infrared spectrum:
 $\mu$CO acid = 1710 cm$^{-1}$
 $\mu$CO ketone = 1660 cm$^{-1}$
Four adjacent aromatic hydrogen atoms : 755 cm$^{-1}$

| Analysis: | C % | H % |
|---|---|---|
| Calculated | 77.13 | 5.75 |
| Found | 76.96 | 6.03 |

Methyl 5-(2'-furoyl)-indan-2-carboxylate

Empirical formula $C_{16}H_{14}O_4$
Melting point = 84°–87° C. (capillary tube)
Infrared spectrum:
 $\mu$CO ester: 1730 cm$^{-1}$
 $\mu$CO ketone: 1640 cm$^{-1}$

| Analysis: | C % | H % |
|---|---|---|
| Calculated | 71.10 | 5.22 |
| Found | 71.11 | 5.09 |

5-(4'-Fluorobenzoyl)-indan-2-carboxylic acid

Empirical formula $C_{17}H_{13}FO_3$
Melting point = 163°–165° C. (capillary tube)

| Acid Value: | Calculated = 197.5 | Found = 197 |
|---|---|---|

Infrared spectrum:
 $\mu$CO acid = 1710 cm$^{-1}$
 $\mu$CO ketone = 1650 cm$^{-1}$

| Analysis: | C % | H % | F % |
|---|---|---|---|
| Calculated | 71.81 | 4.61 | 6.68 |
| Found | 71.95 | 4.48 | 6.49 |

Methyl ester Boiling point at 1.1 torr = 185°–190° C. $n_D^{21} = 1.5800$

5-(2'-Chlorobenzoyl)-indan-2-carboxylic acid

Empirical formula $C_{17}H_{13}Cl\,O_3$
Melting point = 128°–130° C. (capillary tube)

| Acid value: | Calculated = 186 | Found = 183 |
|---|---|---|

Infrared spectrum:
 $\mu$CO acid : 1700 cm$^{-1}$
 $\mu$CO ketone: 1680 cm$^{-1}$

| Analysis: | C % | H % | Cl % |
|---|---|---|---|
| Calculated | 67.89 | 4.36 | 11.79 |
| Found | 67.79 | 4.39 | 11.88 |

The ethyl ester: Melting point at 0.6 to 0.5 torr is 198°–200° C.; $n_D^{21} = 1.588$.

Methyl 5-(2',4'-dichlorobenzoyl)-indan-2-carboxylate

Empirical formula $C_{18}H_{14}Cl_2O_3$
Melting point = 104°–105° C. (capillary tube)
Infrared spectrum:
 $\mu$CO ester = 1730 cm$^{-1}$
 $\mu$CO ketone = 1670 cm$^{-1}$

| Analysis: | C % | H % | Cl % |
|---|---|---|---|
| Calculated | 61.9 | 4.04 | 20.31 |
| Found | 62.06 | 4.08 | 20.37 |

5-Cinnamoyl-indan-2-carboxylic acid

Empirical formula $C_{19}H_{16}O_3$
Melting point = 170°–171° C. (capillary tube)
Infrared spectrum:
 $\mu$CO acid: 1720 cm$^{-1}$
 $\mu$CO ketone: 1655 cm$^{-1}$
NMR spectrum:
 Spread from 11 protons centered around 7.6 ppm
 Peak from 5 indan protons at 3.25 ppm

| Analysis | C % | H % |
|---|---|---|
| Calculated | 78.07 | 5.52 |
| Found | 77.99 | 5.56 |

The ethyl ester $C_{21}H_{20}O_3$
Boiling point at 1.5 torr = 200° C.; $n_D^{19} = 1.6082$.
Infrared spectrum
 $\mu$CO ester = 1740 cm$^{-1}$
 $\mu$CO ketone = 1670 cm$^{-1}$

5-(Cyclohexylcarbonyl)-indan-2-carboxylic acid

Empirical formula $C_{17}H_{20}O_3$
Melting point = 117°–119° C. (capillary tube)
NMR Spectrum:
 One acidic proton at about 8.3 ppm
 A multiplet from 2 aromatic protons centered at around 7.6 ppm
 A doublet from 1 aromatic proton centered on 7.2 ppm
 A peak from 5 indan protons at 3.2 ppm
 A spread from 11 cyclohexyl protons centered around 1.6 ppm

| Analysis: | C % | H % |
|---|---|---|
| Calculated | 74.99 | 7.40 |
| Found | 74.99 | 7.38 |

Methyl ester $C_{18}H_{22}O_3$
Boiling point at 0.5 to 0.6 torr = 140° to 147° C.
Infrared spectrum:
 $\mu$CO ester = 1740 cm$^{-1}$
 $\mu$CO ketone = 1680 cm$^{-1}$
NMR spectrum
 A multiplet from 2 aromatic protons at 7.65 ppm
 A doublet from 1 aromatic proton at 7.2 ppm
 A peak from 3 methoxy protons at 3.7 ppm
 A peak from 5 indan protons at 3.2 ppm
 A spread from 11 cyclohexyl protons at 1.6 ppm

Methyl 5-(2'-thenoyl)-indan-2-carboxylate

Empirical formula $C_{16}H_{14}O_3S$
Boiling point at 1–1.5 torr = 196° to 220° C.
Melting point = 75°–77° C.
Infrared spectrum:
 $\mu$CO ester = 1730 cm$^{-1}$
 $\mu$CO ketone = 1630 cm$^{-1}$
NMR spectrum:
 A multiplet from 4 aromatic protons at 7.7 ppm
 A multiplet from 2 aromatic protons at 7.2 ppm
 A peak from 3 methoxy protons at 3.7 ppm A peak from 3 indan protons at 3.3 ppm

| Analysis: | C % | H % | S % |
|---|---|---|---|
| Calculated | 67.13 | 4.93 | 11.20 |
| Found | 67.05 | 4.89 | 11.09 |

5-(2'-thenoyl)-indan-2-carboxylic acid

Empirical formula $C_{15}H_{12}O_3S$
Melting point=117.5°–119° C. (capillary tube)
Infrared spectrum:
  $\mu CO$ acid: 1700 cm$^{-1}$
  $\mu CO$ ketone: 1630 cm$^{-1}$
NMR spectrum:
  A proton from acidic OH around 11.15 ppm
  A spread from 4 aromatic protons at 7.7 ppm
  A spread from 2 aromatic protons at 7.2 ppm
  A peak from 5 indan protons at 3.4 ppm

| Analysis: | C % | H % | S % |
|---|---|---|---|
| Calculated | 66.15 | 4.44 | 11.78 |
| Found | 66.22 | 4.23 | 11.81 |

Methyl 5-phenacetyl-indan-2-carboxylate

Empirical formula $C_{19}H_{18}O_3$
Melting point=82°–84° C. (capillary tube)
Infrared spectrum:
  $\mu CO$ ester=1730 cm$^{-1}$
  $\mu CO$ ketone=1680 cm$^{-1}$
NMR Spectrum
  A multiplet from 2 aromatic protons=7.7 ppm
  A spread from 6 aromatic protons=7.15 ppm
  A peak from 2 methylene protons=4.1 ppm
  A peak from 3 methoxy protons=3.65 ppm
  A peak from 5 indan protons=3.2 ppm

| Analysis: | C % | H % |
|---|---|---|
| Calculated | 77.54 | 6.15 |
| Found | 77.58 | 6.08 |

5-(2',5'-dichlorobenzoyl)-indan-2-carboxylic acid

Empirical formula $C_{17}H_{12}Cl_2O_3$
Melting point=139°–141° C. (capillary tube)

| Acid Valve: | Calculated = 167 | Found = 166.5 |
|---|---|---|

Infrared spectrum
  $\mu CO$ acid = 1695 cm$^{-1}$
  $\mu CO$ ketone = 1665 cm$^{-1}$
NMR spectrum
  A spread from 1 acidic proton at 8 ppm
  A multiplet from 6 aromatic protons at 7.4 ppm
  A peak from 5 indan protons at 3.25 ppm

| Analysis | C % | H % | Cl % |
|---|---|---|---|
| Calculated | 60.91 | 3.61 | 21.15 |
| Found | 60.96 | 3.60 | 20.99 |

The methyl ester

Empirical Formula $C_{18}H_{14}Cl_2O_3$
Boiling point at 0.6–0.7 torr=200° to 215° C.
Infrared spectrum:
  $\mu CO$ ester: 1740 cm$^{-1}$
  $\mu CO$ ketone: 1670 cm$^{-1}$ NMR spectrum:
  One aromatic proton at 7.6 ppm
  A spreak from 5 aromatic protons at 7.3 ppm
  A peak from 3 methoxy protons at 3.65 ppm
  A peak from 5 indan protons at 3.2 ppm

Methyl 5-nicotinoyl-indan-2-carboxylate

Empirical formula $C_{17}H_{15}NO_3$
Boiling point at 0.6 torr=200° C.
Melting point=68.5°–70.5° C.
Infrared spectrum:
  $\mu CO$ ester=1740 cm$^{-1}$
  $\mu CO$ ketone=1650 cm$^{-1}$
NMR spectrum
  A spread from 1 aromatic proton at 9.1 ppm
  A multiplet from 1 aromatic proton at 9 ppm
  A multiplet from 1 aromatic proton at 8.1 ppm
  A multiplet from 4 aromatic protons at 7.5 ppm
  A peak from 3 methoxy protons at 3.7 ppm
  A peak from 5 indan protons at 3.3 ppm

| Analysis: | C % | H % | N % |
|---|---|---|---|
| Calculated | 72.58 | 5.38 | 4.98 |
| Found | 72.53 | 5.39 | 4.98 |

Methyl 5-(3'-thenoyl)-indan-2-carboxylate

Empirical formula $C_{16}H_{14}O_3S$
Boiling point at 0.9 torr=200°–210° C. Melting point=77.5° to 79° C.
Infrared spectrum:
  $\mu CO$ ester=1740 cm$^{-1}$
  $\mu CO$ ketone=1640 cm$^{-1}$
NMR spectrum
  A multiplet from 1 aromatic proton at 7.9 ppm
  A multiplet from 3 aromatic protons at 7.6 ppm
  A multiplet from 2 aromatic protons at 7.3 ppm
  A peak from 3 methoxy protons at 3.7 ppm
  A peak from 5 indan protons at 3.3 ppm

| Analysis | C % | H % | S % |
|---|---|---|---|
| Calcuated | 67.13 | 4.93 | 11.20 |
| Found | 67.08 | 5.06 | 11.14 |

5-(3'-thenoyl)-indan-2-carboxylic acid

Empirical formula $C_{15}H_{12}O_3S$
Melting point=128.5° to 130° C. (capillary tube)
Infrared spectrum:
  $\mu OH$=3500 to 3100 cm$^{-1}$
  $\mu CO$ acid=1715 cm$^{-1}$
  $\mu CO$ ketone=1650 cm$^{-1}$
NMR spectrum
  A multiplet from 1 aromatic proton at 8 ppm
  A multiplet from 3 aromatic protons at 7.65 ppm
  A multiplet from 2 aromatic protons at 7.35 ppm
  A spread from 5 indan protons at 3.4 ppm

| Analysis: | C % | H % | S % |
|---|---|---|---|
| Calcuated | 66.15 | 4.44 | 11.78 |
| Found | 66.08 | 4.44 | 11.75 |

5-(4'-Aminobenzoyl)-indan-2-carboxylic acid

Empirical formula $C_{17}H_{15}NO_3$
Melting point=212°–213° C. (capillary tube)

Infrared spectrum:
 μNH=3460–3350 cm$^{-1}$
 μCO=1690 cm$^{-1}$
NMR spectrum
 A spread from 5 aromatic protons around 7.4 ppm
 A doublet from 2 aromatic protons around 6.6 ppm
 A spread from 5 indan protons around 3.2 ppm

| Analysis: | C % | H % | N % |
|---|---|---|---|
| Calculated | 72.58 | 5.38 | 4.98 |
| Found | 72.49 | 5.53 | 4.89 |

The methyl ester $C_{18}H_{17}NO_3$
Melting point: 98°–100° C. (capillary tube)
Infrared spectrum
 μNH=3450–3350–3240 cm$^{-1}$
 μCO ester=1730 cm$^{-1}$
 μCO ketone=1640 cm$^{-1}$
NMR Spectrum
 A multiplet from 5 aromatic protons at 7.5 ppm
 A doublet from 2 aromatic protons at 6.6 ppm
 A spread from 2 amine protons at 5.5 ppm
 A peak from 3 methoxy protons at 3.7 ppm
 A spread from 5 indan protons at 3.3 ppm 5-(4'-Phenylbenzoyl)-indan-2-carboxylic acid Empirical formula $C_{23}H_{18}O_3$
Melting point: 187°–189° C. (capillary tube)
Infrared spectrum:
 μCO acid=1700 cm$^{-1}$
 μCO ketone=1645 cm$^{-1}$
Five adjacent aromatic hydrogen atoms=700–750 cm$^{-1}$
NMR spectrum:
 Multiplet from 12 aromatic protons at 7.6 ppm
 Peak from 5 indan protons at 3.35 ppm

| Percentage analysis: | C % | H % |
|---|---|---|
| Calculated | 80.69 | 5.30 |
| Found | 80.43 | 5.43 |

5-(3'-Methoxybenzoyl)-indan-2-carboxylic acid

Empirical formula $C_{18}H_{16}O_4$
Melting point=126°–128° C. (capillary tube)

| Acid Value: Calculated = 188 | Found = 184 |
|---|---|

Infrared spectrum
 μCO acid = 1720 cm$^{-1}$
 μCO ketone = 1680 cm$^{-1}$
NMR spectrum
 A multiplet from 2 aromatic protons at 7.65 ppm
 A multiplet from 5 aromatic protons at 7.3 ppm
 A spread from 1 hydroxylic proton at 10.7 ppm
 A peak from 3 methoxy protons at 3.85 ppm
 A peak from 5 indan protons at 3.4 ppm

| Analysis | C % | H % |
|---|---|---|
| Calculated | 72.96 | 5.44 |
| Found | 73.03 | 5.47 |

The methyl ester $C_{19}H_{18}O_4$
Boiling point at 0.9–1.1 torr=225° to 240° C.

5-(2'-Methoxybenzoyl)-indan-2-carboxylic acid

Empirical formula $C_{18}H_{16}O_4$
Melting point: 128° to 130° C. (capillary tube)
Infrared spectrum:
 μCO acid=1700 cm$^{-1}$
 μCO ketone=1650 cm$^{-1}$
Four adjacent aromatic hydrogen atoms=750 cm$^{-1}$
NMR spectrum:
 A multiplet from 7 aromatic protons between 7 and 7.8 ppm
 A spread from 1 hydroxylic proton at 10.3 ppm
 A peak from 2 methoxy protons at 3.7 ppm
 A spread from 5 indan protons at 3.35 ppm

| Analysis | C % | H % |
|---|---|---|
| Calculated | 72.96 | 5.44 |
| Found | 72.98 | 5.38 |

5-(2'-Furoyl)-indan-2-carboxylic acid

Empirical formula $C_{15}H_{12}O_4$
Melting point=168.5°–170.5° C. (capillary tube)
Infrared spectrum
 μCO acid: 1695 cm$^{-1}$
 μCO ketone: 1630 cm$^{-1}$
NMR spectrum:
 A spread from 1 acid proton at 9.6 ppm
 A multiplet from 3 aromatic protons at 7.8 ppm
 A multiplet from 2 aromatic protons at 7.4 ppm
 A multiplet from 1 aromatic proton at 6.6 ppm
 A spread from 5 indan protons at 3.35 ppm

| Analysis: | C % | H % |
|---|---|---|
| Calculated | 70.29 | 4.72 |
| Found | 70.03 | 5.11 |

5-(3'-Furoyl)-indan-2-carboxylic acid

Empirical formula $C_{15}H_{12}O_4$
Melting point=125°–126.5° C. (capillary tube)
Infrared spectrum:
 μCO acid—1700 cm$^{-1}$
 μCO ketone=1645 cm$^{-1}$
NMR spectrum:
 A spread from 1 acidic proton at 10 ppm
 A multiplet from 1 aromatic proton at 7.95 ppm
 A multiplet from 2 aromatic protons at 7.7 ppm
 A multiplet from 1 aromatic proton at 7.55 ppm
 A multiplet from 1 aromatic proton at 7.35 ppm
 A multiplet from 1 aromatic proton at 6.9 ppm
 A spread from 5 indan protons at 3.4 ppm

| Analysis: | C % | H % |
|---|---|---|
| Calculated | 70.29 | 4.72 |
| Found | 69.86 | 4.93 |

The methyl ester

Empirical formula $C_{16}H_{14}O_4$
Boiling point at 0.8–0.6 torr=140° to 170° C.
Infrared spectrum:
 μCO ester: 1735 cm$^{-1}$
 μCO ketone: 1645 cm$^{-1}$
NMR spectrum:
 A multiplet from 1 aromatic proton at 7.9 ppm A multiplet from 2 aromatic protons at 7.65 ppm
A multiplet from 1 aromatic proton at 7.5 ppm
A multiplet from 1 aromatic proton at 7.3 ppm
A multiplet from 1 aromatic proton at 6.85 ppm
A peak from 3 methoxy protons at 3.75 ppm
A spread from 5 indan protons at 3.3 ppm 5-(4'-Ethoxybenzoyl)-indan-2-carboxylic acid Empirical formula $C_{19}H_{18}O_4$
Melting point: 140°–142° C. (capillary tube)
Infrared spectrum:
  $\mu$CO acid: 1700 cm$^{-1}$
  $\mu$CO ketone: 1645 cm$^{-1}$
NMR spectrum:
  A peak from 1 acidic proton at 11 ppm
  A doublet from 2 aromatic protons at 7.85 ppm
  A multiplet from 2 aromatic protons at 7.6 ppm
  A multiplet from 1 aromatic proton at 7.3 ppm
  A doublet from 2 aromatic protons at 6.85 ppm
  A quadruplet from ethyl group at 4.1 ppm
  A spread from 5 indan protons at 3.35 ppm
  A triplet from ethyl group at 1.5 ppm

| Analysis: | C % | H % |
|---|---|---|
| Calculated | 73.54 | 5.85 |
| Found | 73.16 | 5.88 |

The methyl ester

Empirical formula $C_{20}H_{20}O_4$
Boiling point at 0.8 torr = 225° to 230° C.
Infrared spectrum:
  $\mu$CO ester = 1730 cm$^{-1}$
  $\mu$CO ketone = 1640 cm$^{-1}$ 5-(3',4'-Dichlorobenzoyl)-indan-2-carboxylic acid Empirical formula $C_{17}H_{12}Cl_2O_3$
Melting point = 166°–168° C. (capillary tube)
Infrared spectrum:
  $\mu$CO acid: 1710 cm$^{-1}$
  $\mu$CO ketone: 1655 cm$^{-1}$
NMR spectrum:
  A multiplet from 1 aromatic proton at 7.85 ppm
  A multiplet from 6 protons at 7.5 ppm
  A spread from 5 indan protons at 3.35 ppm

| Analysis: | C % | H % | Cl % |
|---|---|---|---|
| Calculated | 60.91 | 3.61 | 21.15 |
| Found | 60.93 | 3.63 | 21.09 |

The methyl ester

Empirical formula $C_{18}H_{14}Cl_2O_3$
Boiling point at 0.9–1.2 torr = 220°–240° C.
Infrared spectrum:
  $\mu$CO ester: 1745 cm$^{-1}$
  $\mu$CO ketone: 1665 cm$^{-1}$
NMR spectrum:
  A multiplet from 1 aromatic proton at 7.9 ppm
  A multiplet from 5 aromatic protons at 7.5 ppm
  A peak from 3 methoxy protons at 3.8 ppm
  A peak from 5 indan protons at 3.35 ppm 5-(5'-Methyl-2'-thenoyl)-indan-2-carboxylic acid Empirical formula $C_{16}H_{14}O_3S$
Melting point = 165°–166° C. (capillary tube)
Infrared spectrum:
  $\mu$CO: 1710 cm$^{-1}$
NMR spectrum:
  A spread from 1 acid proton at 9.5 ppm
  A multiplet from 2 aromatic protons at 7.65 ppm
  A multiplet from 2 aromatic protons at 7.45 ppm
  A multiplet from 1 aromatic proton at 6.8 ppm
  A spread from 5 indan protons at 3.35 ppm
  A peak from 3 methyl protons at 2.6 ppm

| Analysis: | C % | H % | S % |
|---|---|---|---|
| Calculated | 67.13 | 4.93 | 11.20 |
| Found | 67.10 | 4.99 | 11.08 |

The methyl ester

Empirical formula $C_{17}H_{16}O_3S$
Boiling point at 0.3 torr = 190°–210° C.
Infrared spectrum:
  $\mu$CO ester: 1745 cm$^{-1}$
  $\mu$CO ketone: 1640 cm$^{-1}$
NMR spectrum
  A multiplet from 2 aromatic protons at 7.65 ppm
  A multiplet from 2 aromatic protons at 7.4 ppm
  A multiplet from 1 aromatic proton at 6.8 ppm
  A peak from 3 methoxy protons at 3.7 ppm
  A spread from 5 indan protons at 3.35 ppm
  A peak from 3 methyl protons at 2.55 ppm 5-(5'-Chloro-2'-thenoyl)-indan-2-carboxylic acid Empirical Formula $C_{15}H_{11}Cl\ O_3S$
Melting point = 140°–141° C. (capillary tube)
Infrared spectrum:
  $\mu$CO acid: 1710 cm$^{-1}$
  $\mu$CO ketone: 1630 cm$^{-1}$
NMR spectrum:
  A spread from 1 acid proton at 9.5 ppm
  A multiplet from 2 aromatic protons at 7.6 ppm
  A multiplet from 2 aromatic protons at 7.4 ppm
  A doublet from 1 aromatic proton at 6.95 ppm
  A spread from 5 indan protons at 3.35 ppm

| Analysis: | C % | H % | Cl % | S % |
|---|---|---|---|---|
| Calculated | 58.72 | 3.61 | 11.56 | 10.45 |
| Found | 58.86 | 3.48 | 11.61 | 10.45 |

The methyl ester

Empirical formula $C_{16}H_{13}Cl\ O_3S$
Boiling point at 0.3–0.35 torr = 200°–210° C.
Infrared spectrum:
  $\mu$CO ester: 1740 cm$^{-1}$
  $\mu$CO ketone: 1635 cm$^{-1}$
NMR spectrum:
  A multiplet from 2 aromatic protons at 7.6 ppm
  A multiplet from 2 aromatic protons at 7.4 ppm
  A doublet from 1 aromatic proton at 6.95 ppm
  A peak from 3 methoxy protons at 3.7 ppm
  A spread from 5 indan protons at 3.35 ppm 5-(4'-Acetamidobenzoyl)-indan-2-carboxylic acid Empirical formula $C_{19}H_{17}NO_4$
Melting point = 204°–205° C. (capillary tube)
Infrared spectrum:
  $\mu$NH: 3340 cm$^{-1}$
  $\mu$CO acid: 1720 cm$^{-1}$
  $\mu$CO: 1650 cm$^{-1}$
NMR spectrum:
  A peak from 4 aromatic protons at 7.7 ppm A multiplet from 3 aromatic protons at 7.4 ppm
A spread from 5 indan protons at 3.35 ppm
A peak from 3 methyl protons at 2.2 ppm

| Analysis: | C % | H % | N % |
|---|---|---|---|
| Calculated | 70.58 | 5.30 | 4.33 |
| Found | 70.56 | 5.49 | 4.29 |

The methyl ester

Empirical formula $C_{20}H_{19}NO_4$
Melting point: 139°–140° C. (capillary tube)
Infrared spectrum:
 $\mu$NH: 3250 cm$^{-1}$
 $\mu$CO ester: 1730 cm$^{-1}$
 $\mu$CO: 1650 cm$^{-1}$ Example No. 3

5-(4'-Methoxybenzoyl)-indan-2-carboxylic acid

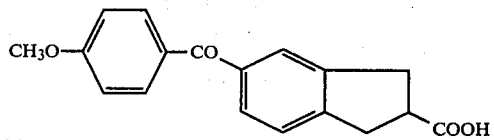

Empirical formula $C_{18}H_{16}O_4$
Molecular weight = 296.31

(a) 4-(4'-Methoxybenzoyl)-1,2-dimethylbenzene

Empirical formula $C_{16}H_{16}O_2$

The following are successively added to a 500 cm$^3$ reaction vessel fitted with a stirrer and cooler: 135 g (1.272 mole) of orthoxylene, 1.27 g of zinc oxide and 108.5 g (0.636 mole) of 4-methoxybenzyl chloride. The mixture is heated to reflux for four hours, the resulting reaction mixture is dissolved in water and soda and extracted with benzene. The benzene extract is dried over anhydrous sodium sulphate, filtered, the filtrate concentrated and the residue distilled. The fraction collected has a boiling point of 185° C. at 0.75 torr.

(b) 4-(4'-methoxybenzoyl)-1,2-bis(bromomethyl)benzene

Empirical formula $C_{16}H_{14}Br_2O_2$

The following are successively added to a 2 liter reaction vessel fitted with a stirrer, a cooler, a dropping funnel and a thermometer: 100.2 g (0.425 mole) of 4-(4'-methoxybenzoyl)-1,2-dimethylbenzene, 166 g (0.425 mole+10%) of N-bromosuccinimide and 565 cm$^3$ of carbon tetrachloride. The mixture is heated to reflux and 17 g of $\alpha,\alpha'$-azobisisobutyronitrile is introduced in small quantities. Reflux is continued for 30 minutes, the precipitate which forms is filtered and the filtrate is concentrated. In this way there is obtained a thick oil which is used as prepared in the next stage.

(c) Ethyl 5-(4'-methoxybenzoyl)-indan-2,2-dicarboxylate

Empirical formula $C_{23}H_{24}O_6$

The following are successively added to a 2 liter reaction vessel equipped with a stirrer, a cooler and a dropping funnel: 210 cm$^3$ of ethyl carbonate, 50.5 g (0.850 mole+10%) of sodium methylate, and 68 g (0.425 mole) of ethyl malonate. A rise in temperature is observed. The reaction is allowed to continue for 30 minutes and then 169 g (0.425 mole) of 4-(4'-methoxybenzoyl)-1,2-bis(bromomethyl)benzene in solution in 425 cm$^3$ of ethyl carbonate is added. The mixture is heated to reflux for nine hours, allowed to cool and diluted with acidified water. The ethyl carbonate phase is deecanted, dried over anhydrous sodium sulphate, filtered and the filtrate concentrate. The crude substance thus obtained is used as it is for the next stage of the process.

(d) 5-(4'-methoxybenzoyl)-indan-2,2-dicarboxylic acid

Empirical formula $C_{19}H_{16}O_6$ 168 g (0.425 mole) of ethyl 5-(4'-methoxybenzoyl)-indane-2,2-dicarboxylate, 1200 cm$^3$ of ethanol, and 119 g (2.125 mole) of potash dissolved in 740 cm$^3$ of water are placed in a 2 liter reaction vessel equipped with a stirrer and cooler. The mixture is heated to reflux for 45 minutes, the alcohol is evaporated, the resulting mixture is diluted with water and the mixture then washed with ether under alkaline conditions. The mixture is then acidified, extracted with ether and the extract dried over anhydrous sodium sulphate, filtered and the filtrate concentrated. A doughy solid is obtained which is used as prepared for the next stage of the process.

(e) 5-(4'-methoxybenzoyl)-indan-2-carboxylic acid

Empirical formula $C_{18}H_{16}O_4$ 77.5 g (0.228 mole) of the crude acid obtained in (d) and 1070 cm$^3$ of concentrated hydrochloric acid are placeed in a 2 liter reaction vessel equipped with a stirrer and cooler. The mixture is heated to reflux for 15 hours. After cooling, the reaction mixture is extracted with diethyl ether, the extract dried over anhydrous sodium sulphate, filtered, and the filtrate concentrated. A doughy solid is obtained which, after recrystallization from ethyl acetate, melts at 149°–151° C. (capillary tube). If difficulty is experienced in purifying the acid by recrystallization, the methyl ester of the acid may first be formed, for example, and purified by distillation (boiling point at 0.67 torr=218° C.) and then hydrolyzed with aqueous alcoholic potash using a known method. The acid obtained is thus more easily able to be purified.

Acid Value:
Theoretical = 189    Found = 186
Infrared spectrum:
$\mu$CO acid:    1710 cm$^{-1}$
$\mu$CO ketone: 1650 cm$^{-1}$

| Analysis: | C % | H % |
|---|---|---|
| Calculated | 72.96 | 5.44 |
| Found | 73.10 | 5.48 |

Example No. 4

N-(2'-hydroxyethyl) 5-benzoyl-indan-2-carboxamide

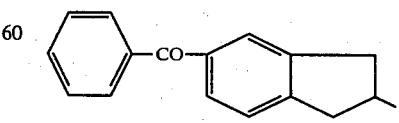

Empirical formula $C_{19}H_{19}NO_3$
Molecular weight = 309.35

6.2 g (0.084 mole+20%) of monoethanolamine dissolved in 30 cm$^3$ of dioxane is placed in a 250 cm$^3$ reaction vessel equipped with a stirrer, a cooler, a dropping funnel and a thermometer. At a temperature of between 15° and 20° C., a solution of 12.2 g (0.042 mole) of 5-benzoyl-indan-2-carboxylic acid chloride (prepared in conventional manner by reacting thionyl chloride with the corresponding acid) in 30 cm³ of dioxane is slowly added. The reaction mixture is stirred for one hour at ambient temperature and then poured into iced, acidified water. A whitish oil separates and finally crystallizes. Upon recrystallization from acetone, a solid

| Analysis: | C % | H % | N % |
|---|---|---|---|
| Calculated | 65.92 | 6.42 | 3.08 |
| Found | 65.88 | 6.30 | 3.10 |

Example No. 6

2'-(N-cinnamoylaminoethyl) 5-benzoyl-indan-2-carboxylate

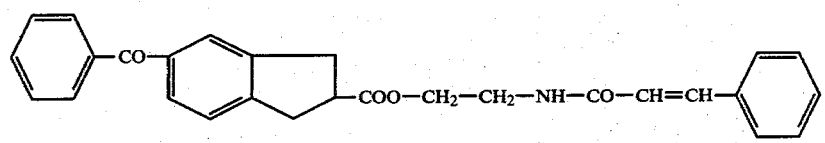

Empirical formula $C_{28}H_{25}NO_4$
Molecular weight = 439.49 which melts at 106°-107° C. (capillary tube) is obtained.
Infrared spectrum:
  $\mu$NH—OH: 3300 cm$^{-1}$
  $\mu$CO: 1640 cm$^{-1}$
Five adjacent aromatic hydrogen atoms: 695–725 cm$^{-1}$

| Analysis: | C % | H % | N % |
|---|---|---|---|
| Calculated | 73.77 | 6.19 | 4.53 |
| Found | 73.89 | 6.16 | 4.44 |

Example No. 5

2'-(N,N-diethylaminoethyl) 5-benzoyl-indan-2-carboxylate

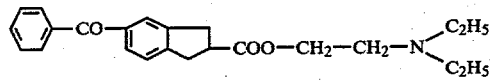

Empirical formula $C_{23}H_{27}NO_3$
Molecular weight = 365.46

The following are added successively to a 250 cm³ reaction vessel equipped with a stirrer, a cooler and a dropping funnel: 11.5 g (0.043 mole) of 5-benzoyl-indan-2-carboxylic acid, 110 cm³ of isopropanol, 7.15 g (0.043 mole+20%) of potassium carbonate and 7.40 g (0.043 mole) of 2-chloroethyldiethylamine hydrochloride dissolved in 70 cm³ of isopropanol. The mixture is heated to reflux for 15 hours. After cooling, the isopropanol is removed under reduced pressure and the resulting mixture diluted with water and washed with ether under acid conditions. The aqueous phase is basified and then extracted with diethyl ether. The extract is dried over sodium sulphate, filtered and the filtrate concentrated. Distillation of the residue gives a thick oil (boiling point at 0.5 torr=210°-220° C.). By forming the oxalate, a solid is obtained which, after recrystallization from a mixture of acetone and ethanol, melts at 141°-143° C. (capillary tube).

Acid value:
Calculated 244    Found 239
Infrared spectrum
  $\mu$CO ester:   1735 cm$^{-1}$
  $\mu$CO ketone:  1655 cm$^{-1}$ The following are successively added to a 250 cm³ reaction vessel equipped with a stirrer and a cooler: 5.55 g (0.029 mole) of N-(2'-hydroxyethyl)cinnamamide, 70 cm³ of benzene, 8.25 g (0.029 mole) of 5-benzoyl-indan-2-carboxylic acid chloride, and 3.1 g (0.029 mole+5%) of triethylamine. The mixture is heated to reflux for six hours. The reaction mixture is then poured into water and extracted with benzene. The extract is dried over anhydrous sodium sulphate, filtered, the filtrate concentrated and the residue obtained recrystallized from a mixture of ethyl acetate and hexane to give a solid which melts at 117.5°-118° C. (capillary tube).
Infrared spectrum
  $\mu$NH: 3280 cm$^{-1}$
  $\mu$CO ester: 1735 cm$^{-1}$
  $\mu$CO: 1650 cm$^{-1}$
Five adjacent aromatic hydrogen atoms: 730–700 cm$^{-1}$
NMR spectrum:
  Spread from 13 aromatic protons+CH=CH' trans proton around 7.5 ppm.
  A doublet from 1 CH=CH trans proton: 6.42 ppm
  A proton from NH: 6.3 ppm
  A triplet from two methylene protons: 4.4 ppm
  A triplet from two methylene protons: 3.8 ppm
  Five indan protons: 3.35 ppm

| Analysis: | C % | H % | N % |
|---|---|---|---|
| Calculated | 76.51 | 5.73 | 3.19 |
| Found | 76.43 | 5.93 | 3.13 |

Example No. 7

4'-Benzoylorthoxylene

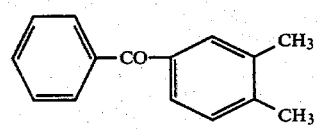

Empirical formula $C_{15}H_{14}O$
Molecular weight = 210.26

As an alternative to the zinc oxide procedure described in the literature, the following procedure may be adopted: in a 250 cm³ reaction vessel equipped with a cooler, a dropping funnel and a nitrogen discharge tube, a Grignard solution is prepared from: 4.7 g (0.234 mole) of magnesium, 43.3 g (0.234 mole) of 4-bromoorthoxylene and 150 cm³ of tetrahydrofurane. When the magnesium has dissolved, 29.8 g (0.212 mole) of benzoyl chloride dissolved in 100 cm³ tetrahydrofurane is added to the solution at 0° C. The mixture is left to stand for one hour at 0° C. and for eighteen hours at ambient temperature and then, after hydrolysis in known manner and extraction with diethyl ether, drying over sodium sulphate, filtration, concentration and distillation of the residue, an oil is obtained, the properties of which agree with those described in the literature.

Example No. 8

5-(3'-Methyl-2'-thenoyl)-indan-2-carboxylic acid

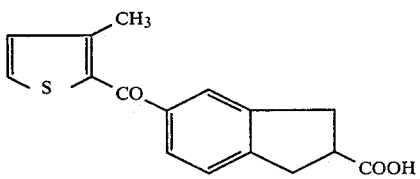

Empirical formula $C_{16}H_{14}O_3S$
Molecular weight = 286.33

(a) Methyl 5-(3'-methyl-2'-thenoyl)-indan-2-carboxylate

Empirical formula $C_{17}H_{16}O_3S$ 18 g (0.139 mole) aluminum chloride is introduced into a 250 cc reactor equipped with a stirrer, a cooler fitted with a calcium chloride trap, a dropping funnel, and a thermometer, and 14.1 g (0.08 mole) methyl indan-2-carboxylate is added drop by drop through the dropping funnel. When this is complete, the temperature reaches 35° C. The mixture is heated slightly for homogenization. Then, 12.8 g (0.08 mole) 3-methylthiophene-2-carboxylic acid chloride are added drop by drop at about 20° C. The mixture is heated gradually to about 70° to 80° C. It is kept at this temperature for 30 minutes then allowed to cool to 40° C. At this time, methylene chloride is added, then the solution obtained is poured into ice water to which hydrochloric acid has been added. The organic phase is decanted, and washed with soda water, then water. It is dried on sodium sulfate, and filtered; the filtrate is concentrated and the residue is distilled. A thick oily fraction, Eb$_{0.7}$ torr: 180°-200° C., is recovered.

Infrared spectrum:
$\nu CO$: 1740 cm$^{-1}$
$\nu CO$: 1640 cm$^{-1}$

NMR Spectrum
clump of 5 aromatic protons centered at about 7.4 ppm
peak of 3 OCH$_3$ protons at 3.4 ppm
peak of 5 indan protons at 3.33 ppm
peak of 3 CH$_3$ protons at 2.4 ppm.

(b) Conversion to 5-(3'-methyl-2'-thenoyl)-indan-2-carboxylic acid

The following are introduced successively into a 250 cc reactor equipped with a stirrer and cooler:
6.7 g (0.0223 mole) of the ester obtained by step (a), dissolved in 30 cc methanol, and
2.8 g (0.05 mole) of potash dissolved in 30 cc methanol.

The mixture is refluxed for an hour. It is concentrated until dry, dissolved in water, and washed with ether in an alkaline medium. The aqueous phase is acidified while cold by hydrochloric acid; a solid precipitates. It is filtered with suction, washed with water, and dried.

By recrystallization in ethyl acetate, a solid melting at 136°-138° C. (capillary tube) is obtained.

Infrared Spectrum
$\nu CO$: 1700 cm$^{-1}$
$\nu CO$: 1635 cm$^{-1}$

NMR Spectrum
clump of aromatic protons centered at about 7.32 ppm
peak of 5 indan protons at about 3.4 ppm
peak of 3 methyl protons at 2.47 ppm
peak of 1 OH proton at about 10.7 ppm.

Acidity Index
Experimental: 195
Calculated: 190

| Percent Analysis | C % | H % | S % |
|---|---|---|---|
| Calculated | 67.13 | 4.93 | 11.20 |
| Experimental | 67.06 | 4.99 | 11.24 |

Example 9

5-(5'-Methyl-2'-furoyl)-indan-2-carboxylic acid

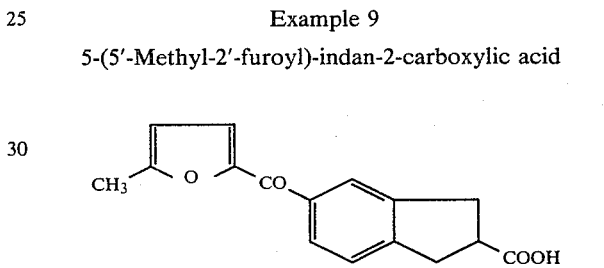

Empirical formula $C_{16}H_{14}O_4$
Molecular weight = 270.27

(a) Methyl 5-(5'-methyl-2'-furoyl)-indan-2-carboxylate

Empirical formula $C_{17}H_{16}O_4$

The following are introduced into a 250 cc reactor equipped with a stirrer, a cooler fitted with a calcium chloride trap, a dropping funnel, and a thermometer:
11.4 g (0.086 mole) aluminum chloride suspended in 30 cc methylene chloride, and
5.5 g (0.0382 mole) 5-methylfuran-2-carboxylic acid chloride dissolved in 30 cc methylene chloride.

The mixture is brought to 20° C. then a solution of 5.6 g (0.318 mole) methyl indan-2-carboxylate in 50 cc methylene chloride is added drop by drop.

The mixture is stirred for two hours at ambient temperature then refluxed for three hours. It is left to stand overnight and poured into a bath of slightly acid ice water. It is extracted with methylene chloride, the extract is washed with soda water and water, then dried on sodium sulfate and filtered; the filtrate is concentrated and the residue distilled. An Eb$_1$ torr: 195°-205° C. fraction is recovered.

Infrared spectrum
$\nu CO$: 1740 cm$^{-1}$
$\nu CO$: 1645 cm$^{-1}$

NMR Spectrum
clump of 4 aromatic protons at about 7.33 ppm
1 aromatic proton at about 6.2 ppm
peak of 5 indan protons at 3.2 ppm
peak of 3 OCH$_3$ protons at 3.7 ppm
peak of 3 CH$_3$ protons at 2.47 ppm (b) Conversion to
5-(5'-methyl-2'-furoyl)-indan-2-carboxylic acid The following are introduced successively into a 50 cc reactor:
2.7 g (0.0095 mole) of the ester obtained by step (a), dissolved in 16.5 cc methanol, and
1.16 g (0.0208 mole) potash dissolved in 16.5 cc water.

The mixture is left to stand at ambient temperature for 48 hours. It is concentrated until dry, dissolved in water, washed with ether in an alkaline medium; then the aqueous phase is acidified. It is extracted with ether, dried on sodium sulfate, and filtered; the filtrate is concentrated. The residue obtained after recrystallization in an ethyl acetate-hexane mixture melts at 128°–130° C. (capillary tube).

Infrared Spectrum
$\nu CO$: 1700 cm$^{-1}$
$\nu CO$: 1635 cm$^{-1}$

NMR Spectrum
1 OH proton at about 10.6 ppm
clump of 4 aromatic protons centered at about 7.5 ppm
1 aromatic proton at about 6.8 ppm
5 indan protons at 3.36 ppm
3 CH$_3$ protons at 2.47 ppm

| Percent Analysis | C % | H % |
|---|---|---|
| Calculated | 71.10 | 5.22 |
| Experimental | 70.99 | 5.16 |

Example 10

5-(4'-dimethylaminobenzoyl)-indan-2-carboxylic acid

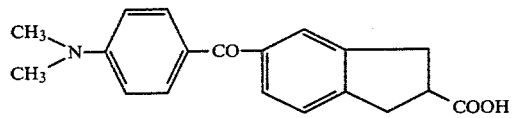

Empirical formula C$_{19}$H$_{19}$NO$_3$
Molecular weight = 309.35

(a) Methyl 5-(4'-dimethylaminobenzoyl)-indan-2-carboxylate

Empirical formula C$_{20}$H$_{21}$NO$_3$
One may proceed according to:
(a) The following are introduced into a 250 cc autoclave, 5 g (0.017 mole) methyl 5-(4'-aminobenzoyl)-indan-2-carboxylate, 100 cc ethanol, and 26 cc formaldehyde (36% in water) in the presence of 2 g Pd/C (5%). The mixture is heated to about 40° C. with stirring after charging the autoclave with hydrogen. After absorption of the theoretical quantity the mixture is filtered to eliminate the catalyst. The ethanol is concentrated in vacuo, dissolved in water, and extracted with ether. It is dried on sodium sulfate and filtered, and the filtrate is concentrated. The residue after recrystallization in an ethyl acetate-diisopropylether mixture melts at 87°–89° C. (capillary tube).

Infrared Spectrum
$\nu CO$: 1740 cm$^{-1}$
$\nu CO$: 1640 cm$^{-1}$
disappearance of NH$_2$ lines NMR Spectrum
doublet, 2 aromatic protons: 7.85 ppm
multiplet, 2 aromatic protons: 7.55 ppm
multiplet, 1 aromatic proton: 7.25 ppm
doublet, 2 aromatic protons: 6.7 ppm
peak, 3 CH$_3$ protons: 3.8 ppm
clump, 5 indan protons: 3.35 ppm
peak, 6 CH$_3$ protons: 3.1 ppm

| Percent Analysis | C % | H % | N % |
|---|---|---|---|
| Calculated | 74.29 | 6.55 | 4.33 |
| Experimental | 74.41 | 6.60 | 4.42 |

(b) The following are introduced into a 125 cc autoclave, 9.6 g (0.068 mole) methyl iodide, 4.9 g (0.034 mole + 5%) K$_2$CO$_3$, 30 cc dimethylformamide and 5 g (0.017 mole) methyl 5-(4'-aminobenzoyl)-indan-2-carboxylate. The mixture is stirred for 24 hours. The dimethylformamide is evaporated in vacuo, dissolved in water, and extracted with ether. The mixture is dried on sulfate, filtered, and the filtrate concentrated. The residue obtained is recrystallized in an ethyl acetate-disopropylether mixture. A substance is obtained whose physical and spectral characteristics are identical to those of the product of the substance obtained according to (a).

(c) Conversion to
5-(4'-dimethylaminobenzoyl)-indan-2-carboxylic acid

In the same manner as specified in Example 8 (b), the following are reacted:
5.6 g (0.0174 mole) methyl 5-(4'-dimethylaminobenzoyl)-indan-2-carboxylate, and
1.95 g (0.0348 mole) potash in 60 cc methanol.

A solid melting at 164°–165° C. (capillary tube) is obtained by recrystallization in ethyl acetate.

Infrared Spectrum
$\nu CO$: 1730 cm$^{-1}$
$\nu CO$: 1620 cm$^{-1}$

NMR Spectrum
clump of 7 aromatic protons centered at about 7.23 ppm
peak of 5 indan protons at 3.3 ppm
peak of 6 CH$_3$ protons at 3.1 ppm

| Percent Analysis | C % | H % | N % |
|---|---|---|---|
| Calculated | 73.77 | 6.19 | 4.53 |
| Experimental | 73.90 | 6.05 | 4.53 |

Example 11

5-(p-methylsulfonylbenzoyl)-indan-2-carboxylic acid

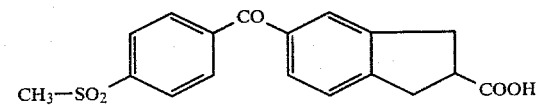

Empirical formula C$_{18}$H$_{16}$O$_5$S
Molecular weight = 344.37

(a) Methyl 5-(p-methylsulfonylbenzoyl)-indan-2-carboxylate is prepared according to Example 8 (a) from
14.5 g (0.107 mole) aluminum chloride,
11 g (0.0475 mole) p-methylsulfonyl benzoic acid chloride, both in 60 cc methylene chloride, and
7 g (0.0397 mole) methyl indan-2-carboxylate in 30 cc methylene chloride.

After concentrating and dissolving the residue in hexane, a solid is obtained which is used in its crude form.

(b) The corresponding acid is prepared according to Example 8 (b) from:

3 g (0.0084 mole) of the ester obtained from (a),
1.1 g (0.02 mole) potash, and
50 cc methanol.

A solid melting at 187°–190° C. (capillary tube) is obtained by recrystallization in ethanol.

Infrared Spectrum
$\nu$CO: 1710 cm$^{-1}$
$\nu$CO: 1670 cm$^{-1}$

NMR Spectrum
clump of 7 aromatic protons centered at about 7.8 ppm
peak of 5 indan protons at 3.33 ppm
peak of 3 CH$_3$ protons at 3.17 ppm Acidity Index
Calculated: 163
Experimental: 155

| Percent Analysis | C % | H % | S % |
| --- | --- | --- | --- |
| Calculated | 62.78 | 4.68 | 9.31 |
| Experimental | 62.90 | 5.01 | 9.17 |

Example 12

5-(p-sulfamidobenzoyl)-indan-2-carboxylic acid

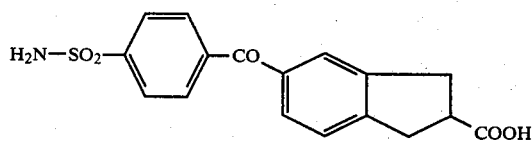

Empirical formula C$_{17}$H$_{15}$NO$_5$S
Molecular weight = 345.36

(a) Methyl 5-(p-chlorosulfonylbenzoyl)-indan-2-carboxylate

Empirical formula C$_{18}$H$_{15}$ClO$_5$S 14.7 g (0.05 mole) methyl 5-(4'-aminobenzoyl)-indan-2-carboxylate are introduced into a 250 cc reactor with a stirrer, thermometer, and dropping funnel. At a temperature between 0°–10° C., 40 cc 24% hydrochloric acid is added, followed by a solution of 3.8 g sodium nitrite in 10 cc water added between 0° and 5° C.

The diazonium salt formed in this way is then added at about 15° C. to a stirred mixture of:

80 cc acetic acid saturated with sulfur dioxide and
2.8 g cupric chloride dissolved in 5 cc water.

The mixture is allowed to return to ambient temperature, heated to about 40° C. to finish the reaction, and left to stand overnight. The next day it is dissolved in ice water and the solid which precipitates is filtered with suction. The substance obtained is checked by NMR and IR spectrography.

(b) Conversion to methyl 5-(p-sulfamidobenzoyl)-indan-2-carboxylate

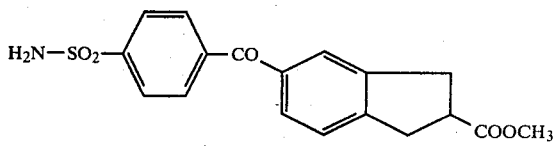

Empirical formula C$_{18}$H$_{17}$NO$_5$S
Molecular weight = 359.40

The following are introduced into a 500 cc reactor with stirrer, cooler, and dropping funnel:

15.6 g (0.041 mole) of the derivative obtained in step (a), and
150 cc chloroform.

Then, while stirring vigorously, 100 cc 15% ammonia are added. The mixture is stirred for one hour and a half at ambient temperature. It is dissolved in water and chloroform. The chloroform phase is decanted, dried on sodium sulfate, filtered, and concentrated.

A solid melting at 147°–149° C. (capillary tube) is obtained by recrystallizing the residue in an ethyl acetate-diisopropyl ether mixture.

Infrared Spectrum
$\nu$NH: 3400–3320 cm$^{-1}$
$\nu$CO: 1745 cm$^{-1}$
$\nu$CO: 1660 cm$^{-1}$ NMR Spectrum
clump of 7 aromatic protons at about 7.66 ppm
peak of 2 NH$_2$ protons at 6.1 ppm
peak of 3 OCH$_3$ protons at 3.7 ppm
peak of 5 indan protons at 3.3 ppm (c) Conversion to the corresponding acid Starting from:

11 g (0.0306 mole) of ester obtained by (b) dissolved in 100 cc ethanol, and
3.4 g (0.06 mole) potash dissolved in 100 cc water, the ester is converted to the acid under the conditions set forth in Example 8 (b).

After recrystallizing the product obtained in an acetic acid-water mixture, a solid melting at 157°–158° C. (capillary tube) is obtained.

Infrared Spectrum
$\nu$NH: 3320 cm$^{-1}$
$\nu$CO: 1720 cm$^{-1}$
$\nu$CO: 1650 cm$^{-1}$ NMR Spectrum
clump of 7 aromatic protons at about 7.6 ppm
peak of 2 NH$_2$ protons at about 6.6 ppm
1 OH proton at about 10.5 ppm
5 indan protons at 3.4 ppm

| Percent Analysis | C % | H % | N % | S % |
| --- | --- | --- | --- | --- |
| Calculated | 59.12 | 4.38 | 4.06 | 9.28 |
| Experimental | 59.38 | 4.14 | 4.09 | 9.24 |

Example 13

5-(p-dimethylaminosulfonylbenzoyl)-indan-2-carboxylic acid

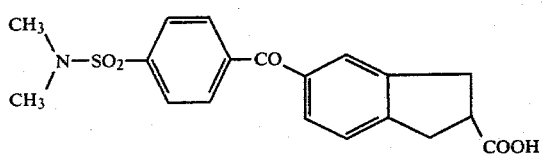

Empirical formula $C_{19}H_{19}NO_5S$
Molecular weight = 373.41

(a) Methyl 5-(p-dimethylaminosulfonylbenzoyl)-indan-2-carboxylate

Empirical formula $C_{20}H_{21}NO_5S$

This is prepared according to Example 12 (b) from:
- 28 g (0.074 mole) methyl 5-(p-chlorosulfonylbenzoyl)-indan-2-carboxylate in 90 cc chloroform, and
- 34 cc (0.148 mole) of a 40% dimethylamine solution in water.

(b) Conversion to the corresponding acid

The conversion is carried out according to Example 12 (c) from:
- 21 g (0.0545 mole) of crude ester obtained in step (a) in 200 cc water, and
- 6.15 g (0.11 mole) potash in 200 cc ethanol.

After recrystallization in an ethyl acetate-hexane mixture, a solid melting at 144°–145° C. (capillary tube) is obtained.

Infrared Spectrum
  $\nu$CO: 1700 cm$^{-1}$
  $\nu$CO: 1660 cm$^{-1}$

NMR Spectrum
  peak of 4 aromatic protons at 7.97 ppm
  clump of 3 aromatic protons at 7.53 ppm
  peak of 5 indan protons at 3.3 ppm
  peak of 6 CH$_3$ protons at 2.8 ppm

| Percent Analysis: | C % | H % | N % | S % |
|---|---|---|---|---|
| Calculated | 61.11 | 5.13 | 3.75 | 8.57 |
| Experimental | 61.09 | 5.19 | 3.71 | 8.64 |

Example 14

Ethyl 5-(4'-acetamido-3'-chlorobenzoyl)-indan-2-carboxylate

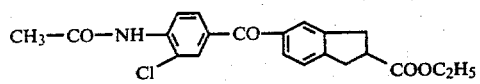

Empirical formula $C_{21}H_{20}ClNO_4$
Molecular weight = 385.8

The following are introduced into a 250 cc reactor with a stirrer, cooler, dropping funnel and thermometer:
- 8.8 g (0.025 mole) of ethyl 5-(p-acetamidobenzoyl)-indan-2-carboxylate, and
- 30 cc acetic acid 40 cc acetic acid saturated with chlorine are added drop by drop at a temperature of about 10° C. The initial suspension disappears gradually. It is allowed to return to ambient temperature over one hour, then the acetic acid is concentrated in vacuo. An oil is obtained which, by recrystallization in an ethyl acetate-hexane mixture, gives a solid melting at 126°–127° C. (capillary tube).

Infrared Spectrum
  $\nu$NH: 3350 cm$^{-1}$
  $\nu$CO: 1740 cm$^{-1}$
  $\nu$CO: 1690 cm$^{-1}$
  $\nu$CO: 1650 cm$^{-1}$ NMR Spectrum
  1 aromatic proton at about 8.6 ppm
  clump of 6 aromatic protons centered at about 7.5 ppm
  quadruplet of 2 CH$_2$ protons at about 4.2 ppm
  5 indan protons at 3.33 ppm
  peak of 3 CH$_3$ protons at 2.23 ppm
  peak of 3 CH$_3$ protons at 1.3 ppm

| Percent Analysis | C % | H % | Cl % | N % |
|---|---|---|---|---|
| Calculated | 65.37 | 5.23 | 9.19 | 3.63 |
| Experimental | 65.50 | 5.22 | 9.15 | 3.63 |

Example 15

5-(4',5'-dichloro-2'-thenoyl)-indan-2-carboxylic acid

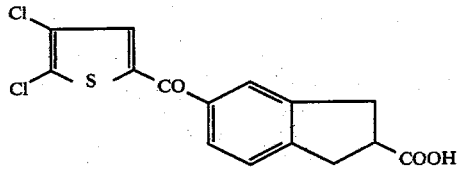

Empirical formula $C_{15}H_{10}Cl_2O_3S$
Molecular weight = 341.20

The following are introduced into a 250 cc reactor equipped with a stirrer, a cooler, a dropping funnel, and a tube for bubbling gas into the reaction mixture:
- 5.2 g (0.017 mole) 5-(5'-chloro-2'-thenoyl)-indan-2-carboxylic acid.

27 cc acetic acid, saturated with chlorine, is added at about 15° C. The mixture is then heated in a water bath at about 75° C., bubbling chlorine through the reaction mixture. After cooling a solid is isolated by filtering with suction. The latter, recrystallized in ethyl acetate, has a melting point which stabilizes at 190°–192° C. (capillary tube).

Infrared Spectrum
  $\nu$CO: 1720 cm$^{-1}$
  $\nu$CO: 1650 cm$^{-1}$

NMR Spectrum
  clump of 3 indan protons plus 1 thiophene proton centered at about 7.5 ppm
  peak of 5 indan protons at 3.33 ppm

| Percent Analysis | C % | H % | Cl % | S % |
|---|---|---|---|---|
| Calculated | 52.80 | 2.95 | 20.78 | 9.40 |
| Experimental | 52.86 | 2.98 | 20.82 | 9.48 |

Example 16

2'-(N,N-diethylaminoethyl) 5-(2'-thenoyl)-indan-2-carboxylate

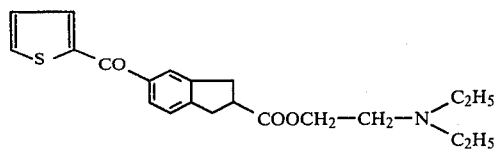

Empirical formula $C_{21}H_{25}NO_3S$
Molecular weight = 371.48

(a) The following are introduced successively into a 500 cc reactor equipped with a stirrer, a cooler, and dropping funnel:
- 27.1 g (0.1 mole) of 5-(2'-thenoyl)-indan-2-carboxylic acid,
- 200 cc isopropanol,
- 16.6 g (0.1 mole+20%) potassium carbonate,
- 17.2 g (0.1 mole) chloroethyl diethylamine hydrochloride, and
- 150 cc isopropanol.

The mixture is refluxed for 15 hours. It is concentrated until dry, dissolved in water, and dilute hydrochloric acid, and washed in ether in an acid medium. The aqueous phase is passed in an alkaline medium and extracted with ether. It is dried on sodium sulfate and filtered, then the filtrate is concentrated.

The residue is distilled and an $Eb_{0.7-0.8\ torr}$: 230°–240° C. fraction is recovered.

Infrared Spectrum
$\nu CO$: 1740 cm$^{-1}$
$\nu CO$: 1650 cm$^{-1}$

NMR Spectrum
  clump of 6 aromatic protons at about 7.47 ppm
  triplet of 2 $CH_2$ protons at about 4.2 ppm
  peak of 5 indan protons at about 3.33 ppm
  clump of 6 $CH_2$ protons at about 2.7 ppm
  triplet of 6 $CH_3$ protons at about 1.07 ppm (b) Conversion to the hydrochloride: $C_{21}H_{26}ClNO_3S$
Mol. wt.=407.9

According to known techniques, a solid melting at 157°–158° C. (capillary tube) is obtained after recrystallization in ethanol.

| Acidity Index | | | | | |
|---|---|---|---|---|---|
| Experimental: | 132 | | | | |
| Calculated: | 137 | | | | |
| Infrared Spectrum | | | | | |
| —$\nu CO$: | 1745 cm$^{-1}$ | | | | |
| —$\nu CO$: | 1630 cm$^{-1}$ | | | | |

| Percent Analsysi (Hydrochloride) | C % | H % | Cl % | N % | S % |
|---|---|---|---|---|---|
| Calculated | 61.83 | 6.43 | 8.69 | 3.43 | 7.86 |
| Experimental | 61.86 | 6.57 | 8.56 | 3.40 | 7.89 |

Example 17

2'-(N,N-diethylaminoethyl) 5-(2'-furoyl)-indan-2-carboxylate

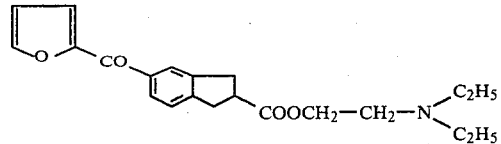

Empirical formula $C_{21}H_{25}NO_4$
Molecular weight = 355.42

This compound is prepared according to Example 16 from:
- 21.4 g (0.0835 mole) 5-(2'-furoyl)-indan-2-carboxylic acid,
- 14.2 g (0.0835 mole+20%) potassium carbonate, and
- 14.4 g (0.0835 mole) chloroethyldiethylamine hydrochloride.

An $Eb_{0.5-0.4\ torr}$: 200°–220° C. fraction is recovered by distillation.

Infrared Spectrum
$\nu CO$: 1740 cm$^{-1}$
$\nu CO$: 1650 cm$^{-1}$

NMR Spectrum
  clump of 3 aromatic protons at about 7.83 ppm
  clump of 2 aromatic protons at about 7.3 ppm
  1 aromatic proton at about 6.53 ppm
  clump of 2 $CH_2$ protons at about 4.1 ppm
  peak of 5 indan protons at 3.33 ppm
  clump of 6 $CH_2$ protons at about 2.7 ppm
  clump of 6 $CH_3$ protons at about 1.07 ppm Conversion to hydrochloride: $C_{21}H_{26}ClNO_4$ After recrystallization in an ethyl acetate-ethanol mixture, a solid melting at 165°–166.5° C. (capillary tube) is obtained.

| Acidity Index | | | | |
|---|---|---|---|---|
| Calculated: | 143 | | | |
| Experimental: | 142 | | | |

| Percent Analysis (Hydrochloride) | C % | H % | Cl % | N % |
|---|---|---|---|---|
| Calculated | 64.36 | 6.69 | 9.05 | 3.57 |
| Experimental | 64.44 | 6.49 | 8.98 | 3.53 |

EXAMPLE 18

N-[2'-(N',N'-diethylaminoethyl)] 5-benzoyl-indan-2-carboxamide

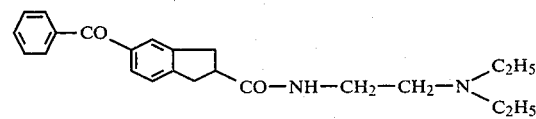

Empirical formula $C_{23}H_{28}N_2O_2$
Molecular weight = 364.47

The following are introduced into a 250 cc reactor with a stirrer, a cooler, a dropping funnel, and a thermometer:
- 25.5 g (0.2 mole+10%) of 2-(N'N'-diethylamino)ethylamine, and
- 50 cc dioxane.

A solution of 30.2 g (0.1 mole) 5-benzoyl-indan-2-carboxylic acid chloride in 50 cc dioxane is added at a temperature between 10° and 20° C.

The mixture is allowed to return to ambient temperature, then stirred at this temperature for an hour. The dioxane is concentrated in vacuo, dissolved in ice water and extracted with ether in an alkaline medium. The ether extract is dried on sulfate, filtered, and the filtrate is concentrated. An oil is obtained on which an oxalate is made.

After recrystallization in an acetone-alcohol mixture, a melting point of 153°–154° C. (capillary tube) is obtained.

Acidity Index
Calculated: 246
Experimental: 226
Infrared Spectrum
—νCO: 1660 cm$^{-1}$

| Percent Analysis ($C_{25}H_{30}N_2O_6$) | C % | H % | N % |
|---|---|---|---|
| Calculated | 66.07 | 6.65 | 6.17 |
| Experimental | 66.10 | 6.50 | 6.18 |

EXAMPLE 19

N-[2'-(N',N'-diethylaminoethyl)] 5-(2'-thenoyl)-indan-2-carboxamide

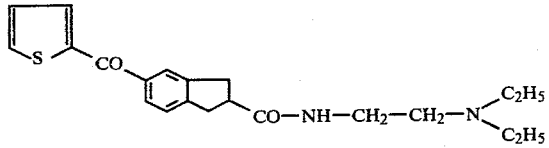

Empirical formula $C_{21}H_{26}N_2O_2S$
Molecular weight = 370.51

This compound is prepared according to Example 18 from:
9.4 g (0.03 mole) 5-(2'-thenoyl)-indan-2-carboxylic acid chloride,
7.7 g (0.066 mole) of 2-(N,N-diethylamino)ethylamine, and
120 cc dioxane.

By passage with oxalate, one obtains, after recrystallization in acetone, a solid melting at 110°–112° C. (capillary tube).

Acidity Index
Calculated: 243
Experimental: 247
Infrared Spectrum
—νCO: 1630 cm$^{-1}$
NMR Spectrum
- clump of 6 aromatic protons at about 7.4 ppm
- clump of 5 indan +8 $CH_2$ protons at about 3.33 ppm
- triplet of 6 $CH_3$ protons at about 1.27 ppm

| Percent Analysis | C % | H % | N % | S % |
|---|---|---|---|---|
| Calculated | 59.98 | 6.13 | 6.09 | 6.96 |
| Experimental | 59.95 | 6.26 | 5.96 | 7.06 |

EXAMPLE 20

N-[2'-(N',N'-diethylaminoethyl)] 5-(2',5'-dichlorobenzoyl)-indan-2-carboxamide

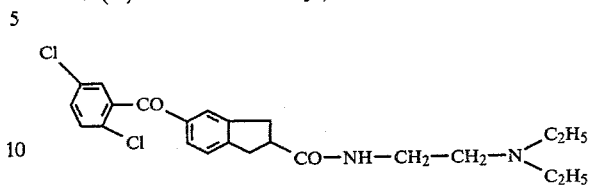

Empirical formula $C_{23}H_{26}Cl_2N_2O_2$
Molecular weight = 433.38

This compound is prepared according to Example 18 from:
17.6 g (0.048 mole) 5-(2'5'-dichlorobenzoyl)-indan-2-carboxylic acid chloride,
13.9 g (0.12 mole) 2-(N,N-diethylamino)ethylamine, and
80 cc dioxane.

A solid melting at 103°–104° C. (capillary tube) is obtained by passage with oxalate and after recrystallization in acetone.

Acidity Index
Calculated: 216
Experimental: 206
Infrared Spectrum
—νCO: 1670 cm$^{-1}$
NMR Spectrum
- clump of 6 aromatic protons centered about 7.46 ppm
- clump of 5 indan +8 $CH_2$ protons at about 3.43 ppm
- triplet of 6 $CH_3$ protons at about 1.33 ppm
- 1 NH proton at about 8.3 ppm

| Percent Analysis ($C_{25}H_{28}Cl_2N_2O_6$) | C % | H % | N % | Cl % |
|---|---|---|---|---|
| Calculated | 57.37 | 5.39 | 5.35 | 13.55 |
| Experimental | 57.38 | 5.48 | 5.39 | 13.56 |

The following clinical experimentation was carried out to clinically test various compounds in accordance with the present invention for their anti-inflammatory, analgesic and platelet aggregation or clumping inhibition activities.

Experiment A

The following case studies relate to the anti-inflammatory activity associated with the oral administration of 5-(5'-methyl-2'-thenoyl)-indan-2-carboxylic acid.

Case 1

Name: MIRT . . . , C.
Age: 40
Sex: F
Diagnosis: Seropositive, classic, rheumatoid polyarthritis, radioclinical stage IV
Treatment: 600 mg/day for 3 weeks
Results: Decrease in morning stiffness and peripheral pain. Improved mobility.
Biologically: decrease in erythrocyte sedimentation rate (ESR).
Tolerance: Very good clinical and biological tolerance.
Conclusion: Good result.

Case 2

Name: DUM . . . , M.

Age: 70
Sex: F
Diagnosis: Ankylosing spondylarthritis with signs of peripheral joint inflammation
Treatment: 600 mg/day for 3 weeks
Results: As effective as phenylbutazone. Good mobility and decrease in articular perimeters. Good analgesic effect.
Tolerance: Good clinical and biological tolerance.
Conclusion: Good result.

Case 3

Name: PER . . . , P.
Age: 58
Sex: M
Diagnosis: Psoriatic peripheral rheumatism
Treatment: 600 mg/day for 15 days
Results: Decrease in morning pain, decrease in articular perimeter, decrease in local heat.
Tolerance: Good clinical and biological tolerance.
Conclusion: Very good result.

Experiment B

The following case studies relate to the analgesic activity associated with the oral administration of methyl 5-(4'-dimethylaminobenzoyl)-indan-2-carboxylate.

Case 1

Name: GAR . . . , J. P.
Age: 65
Sex: M
Diagnosis: Painful episode against a background of arthrosis of the cervical spine
Treatment: 600 mg/day for 3 weeks
Results:
  Time taken to relieve pain: 30 minutes
  Length of relief: 4 hours
Tolerance:
  Clinical: NAD (Nothing Abnormal Discovered)
  Biological: NAD
Conclusion: Good result Case 2

Name: BAR . . . , F.
Age: 50
Sex: F
Diagnosis: Pains in the right hip when pressure applied, secondary to aseptic osteonecrosis
Treatment: 600 mg/day for 15 days
Results:
  Time to relieve pain: less than 15 minutes
  Length of relief: 4 hours
Tolerance:
  Clinical: NAD
  Biological: NAD
Conclusion: Very good result Case 3

Name: GAS . . . , J. F.
Age: 55
Sex: M
Diagnosis: Arthrosis of the right hip resembling Paget's Disease
Treatment: 600 mg/day for 15 days
Results:
  Time to relieve pain: 30 minutes
  Length of relief: 2 hours Tolerance:
  Clinical: NAD
  Biological: NAD
Conclusion: Good result Experiment C The following case studies relate to the platelet anti-aggregation activity associated with the oral administration of 2'-(N,N-diethylaminoethyl) 5-(2'-thenoyl)-indan-2-carboxylate.

Case 1

Name: PUB . . . , F.
Age: 25
Sex: M
Aggregation with collagen before treatment: 100%
  1 h after taking 200 mg: 0%
  3 h after taking 200 mg: 0%
Inhibition of second phase of aggregation with ADP
Aggregation with collagen 24 hours after the last dose: 10%

Case 2

Name: TH . . . , J. P.
Age: 24
Sex: M
Aggregation with collagen before treatment: 100%
  1 h after taking 200 mg: 10%
  3 h after taking 200 mg: 10%
Second phase of aggregation with ADP: 0%
Aggregation with collagen 24 hours after last dose: 15%

Case 3

Name: BEL . . . , C.
Age: 25
Sex: M
Aggregation with collagen before treatment: 100%
  1 h after taking 200 mg: 0%
  3 h after taking 200 mg: 0%
Inhibition of second phase of aggregation with ADP
Aggregation with collagen 24 hours after last dose: 0%

It will be obvious to those skilled in the art that various changes may be made without departing from the scope of the invention and the invention is not to be considered limited to what is described in the specification.

What is claimed is:

1. A 5-substituted indan-2-carboxylic acid or functional derivative thereof having the formula

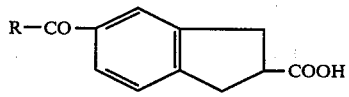

in which R is selected from the group consisting of cyclohexyl, phenyl, phenyl-alkenyl, phenyl-alkyl, and phenyl substituted by a substituent selected from the group consisting of halogen atoms, alkyl, alkoxy, acetamido, amino, dialkylamino, nitro, phenyl, alkylsulfonyl, dialkylaminosulfonyl and sulfamido groups, in the free form or a therapeutically acceptable salt or amide thereof, or a therapeutically acceptable ester selected from the group consisting of alkyl, dialkylaminoalkyl and cinnamoylamidoalkyl carboxylic acid esters.

2. The compound of claim 1 wherein said therapeutically acceptable amide is selected from the group consisting of the dihydro, 2-hydroxyethyl and dialkylaminoalkyl carboxamides.

3. The compound of claim 1 comprising the acid in which R is phenyl.

4. The compound of claim 1 comprising the methyl ester in which R is phenyl.

5. The compound of claim 1 comprising the dialkylaminoalkyl ester in which R is phenyl.

6. The compound of claim 1 wherein R is a phenyl radical substituted by at least one substituent selected from the group consisting of the halogen atoms and the acetamido, dialkylamino, alkylsulfonyl, dialkylaminosulfonyl and sulfamido groups.

7. The compound of claim 6 wherein R is a phenyl radical substituted by at least one substituent selected from the group consisting of chlorine, and the acetamido, dimethylamino, methylsulfonyl, dimethylsulfonyl and sulfamido groups.

8. The compound of claim 1 in the form of a therapeutically acceptable amide wherein said amide comprises the dialkylaminoalkyl carboxamide.

9. The therapeutic composition for combatting inflammation and pain comprising an anti-inflammatory or analgesic amount of a compound in accordance with claim 1 and a pharmaceutically acceptable excipient therefor.

10. The composition in accordance with claim 9 wherein said compound is the acid in which R is phenyl.

11. The composition in accordance with claim 9 in unit dosage form, each unit dose comprising from 50 to 500 mg of said compound.

12. The composition in accordance with claim 10 in unit dosage form, each unit dose comprising from 50 to 500 mg of said compound.

* * * * *